United States Patent
Aalders et al.

(10) Patent No.: US 9,814,811 B2
(45) Date of Patent: Nov. 14, 2017

(54) BREAST PUMP SYSTEM WITH ACTUATOR

(71) Applicant: KONINKLIJKE PHILIPS N.V., Eindhoven (NL)

(72) Inventors: Arnold Aalders, Waalwijk (NL); Godefridus Gertruda Willem Beulen, Venlo (NL); Hassan El Barakat, Eindhoven (NL); Theodorus Johannes Adrianus Maria Den Bekker, Horst (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/398,828

(22) PCT Filed: Jun. 6, 2013

(86) PCT No.: PCT/EP2013/061669
§ 371 (c)(1),
(2) Date: Nov. 4, 2014

(87) PCT Pub. No.: WO2014/044423
PCT Pub. Date: Mar. 27, 2014

(65) Prior Publication Data
US 2015/0190560 A1 Jul. 9, 2015

Related U.S. Application Data

(60) Provisional application No. 61/704,702, filed on Sep. 24, 2012.

(30) Foreign Application Priority Data

Sep. 24, 2012 (EP) .................................. 12185580

(51) Int. Cl.
*A61M 1/06* (2006.01)

(52) U.S. Cl.
CPC .............. *A61M 1/062* (2014.02); *A61M 1/06* (2013.01); *A61M 2205/18* (2013.01);
(Continued)

(58) Field of Classification Search
CPC ............ A61M 1/06; A61M 2205/8206; A61M 2205/50; A61M 2205/8212; A61M 1/0027
(Continued)

(56) References Cited

U.S. PATENT DOCUMENTS 4,740,202 A 4/1988 Stacey et al.
6,045,529 A 4/2000 Nuesch
(Continued)

FOREIGN PATENT DOCUMENTS

JP 2925241 5/1999
JP 2000107280 A 4/2000

*Primary Examiner* — Phillip Gray

(57) ABSTRACT

The present application relates to a breast pump system comprising a vacuum pump, an actuator for driving the vacuum pump, and a power supply for supplying electrical power to a plurality of components including the actuator, and also to a method for use in such as system. An output voltage of the power supply is detected, and in response to the detected output voltage being less than a first threshold voltage, the supply of electrical power to a predetermined one of the plurality of components is suspended. Then, if the detected output voltage recovers to a level above a second threshold value, the supply of electrical power is resumed.

12 Claims, 6 Drawing Sheets

(52) U.S. Cl.
CPC ..... *A61M 2205/33* (2013.01); *A61M 2205/70* (2013.01); *A61M 2205/8212* (2013.01)

(58) Field of Classification Search
USPC ............................................ 604/73–76, 514
See application file for complete search history.

(56) References Cited

U.S. PATENT DOCUMENTS

| | | | |
|---|---|---|---|
| 6,090,065 A | 7/2000 | Giles | |
| 6,673,036 B1* | 1/2004 | Britto | A61M 1/06 604/346 |
| 8,579,884 B2* | 11/2013 | Lanier, Jr. | A61M 5/14224 604/132 |
| 2008/0275386 A1 | 11/2008 | Myers | |
| 2010/0121264 A1 | 5/2010 | Bryan et al. | |
| 2010/0121277 A1* | 5/2010 | Fehr | A61M 5/142 604/151 |
| 2011/0060281 A1* | 3/2011 | Aeschlimann | A61M 5/14244 604/151 |
| 2011/0270162 A1 | 11/2011 | Guo | |

* cited by examiner

BREAST PUMP SYSTEM WITH ACTUATOR

CROSS-REFERENCE TO PRIOR APPLICATIONS

This application is the U.S. National Phase application under 35 U.S.C. §371 of International Application No. PCT/EP2013/061669, filed on Jun. 6, 2013 which claims the benefit of U.S. Provisional Patent Application No. 61/704702, filed on Sep. 24, 2012, and EP application No. 12185580.3, filed on Sep. 24, 2012. These applications are hereby incorporated by reference herein.

FIELD OF THE INVENTION

The present invention relates to breast pumps. More particularly, the present invention relates to interrupting the supply of electrical power to a predetermined one of a plurality of components in a breast pump system.

BACKGROUND OF THE INVENTION

Breast pumps are used by mothers to express breast milk at a convenient time, to be stored for later consumption by their child. The breast pump operates by generating a vacuum to mimic the feeding action of the child. Conventional breast pumps can be categorised as mechanical, in which a user manually operates a vacuum pump in order to generate the required vacuum, or electrical, in which a vacuum pump is driven by an electric motor. It is known that electrical systems in breast pumps could shutdown unexpected and uncontrolled.

In electrical breast pump systems it is generally desirable to improve the reliability of such systems. It is also desirable to reduce power consumption, for instance to maximise battery life.

SUMMARY OF THE INVENTION

It is an object of the invention to provide a breast pump system which substantially alleviates or overcomes one or more of the problems mentioned above.

According to the present invention, there is provided a breast pump system comprising a pump unit, an actuator for driving the pump unit, a power supply arranged to supply electrical power to a plurality of components including the actuator, a voltage detecting module arranged to detect an output voltage of the power supply, and a power interrupt module arranged to suspend the supply of the electrical power to a predetermined one of the plurality of components in response to the detected output voltage falling below a first threshold voltage, and resume the supply of the electrical power to the predetermined one of the plurality of components in response to the detected output voltage recovering above a second threshold voltage.

The above approach has the advantage of improving the reliability of an electrical breast pump system. Furthermore, an uncontrolled shutdown of the breast pump system due to failure of the actuator may be prevented.

The breast pump system may further comprise a switch connected between the power supply and the actuator, wherein the power interrupt module may be arranged to suspend the supply of the electrical power to the actuator by opening the switch, to disconnect the actuator from the power supply. This approach can be used in non-PWM systems to isolate the actuator from the power supply.

The power supply may be arranged to supply the electrical power to the actuator using pulse width modulation PWM. Furthermore, the power interrupt module may be arranged to suspend the supply of the electrical power to the actuator by setting the PWM duty cycle to zero. In PWM-controlled systems, this approach has the advantage that additional components to isolate the actuator are not required, since the actuator can be disconnected from the power supply by holding open the same switch that is used for PWM control, for example a junction transistor or a Field Effect Transistor (FET).

The power interrupt module may include an analogue-to-digital converter ADC for measuring voltages within a predetermined input voltage range, and the breast pump system may further comprise a voltage adapting module for adapting the output voltage to an adapted voltage lying within the input voltage range of the ADC, wherein the power interrupt module may be arranged to detect the output voltage falling below the first threshold voltage by detecting the adapted voltage falling below a corresponding adapted threshold voltage. Adapting the voltage in this way can allow the use of ADCs that have an adapted voltage input range.

The voltage adapting module may comprise first and second resistors connected in series between the output voltage and a first reference voltage to obtain the adapted voltage at a node between the first and second resistors. This offers a low-cost solution for adapting the voltage.

The voltage adapting module may further comprise a capacitor connected between a second reference voltage and the node between the first and second resistors, to filter the adapted voltage. Filtering the adapted voltage can be advantageous, for example to prevent the voltage adapting module from acting on a small/short voltage peak or dip.

The output voltage may be a voltage supplied to the actuator. Alternatively, the output voltage may be a voltage supplied to one or more other components in the breast pump system that are also supplied with electrical power by the power supply, in which case the first threshold voltage may be higher than a minimum operating voltage required by the one or more other components. When the power supply also powers other components as well as the actuator, monitoring a voltage supplied to the other components and setting a corresponding threshold can ensure that during a motor current spike, the actuator can be isolated before the power supply voltage decreases to a level that could cause system instability.

The one or more other components may include a valve for releasing a vacuum generated by the vacuum pump, a voltage stabilising module, and/or a pulse width modulation PWM controller for controlling the actuator. When the same power supply also provides a release valve, voltage stabilising module, and/or PWM controller with electrical power, isolating the actuator when a voltage drop is detected can improve the system stability by allowing the power supply to continue to supply power stably to the release valve, the voltage stabilising module and PWM controller. This is particularly advantageous in the case of the release valve, failure of which could lead to a high vacuum to build up at the breast.

The power interrupt module may be arranged to sample the output voltage with a sampling rate higher than 1000 samples per second. This can allow the actuator to be switched off quickly after the output voltage has reduced beneath the first threshold voltage. Furthermore, this can also allow the power interrupt module to reconnect the actuator rapidly after the output voltage has recovered above the second threshold voltage.

The breast pump system may further comprise an error indication module arranged to indicate an error condition in response to the detected output voltage. The error indication can inform a user that the actuator is nearing the end of its lifetime, allowing the user time to replace the motor or entire breast pump system before failure occurs. For example, in a direct current DC brushed electric motor the decrease in output voltage can occur towards the end of the motor life, as the carbon brushes are heavily worn down and their resistance decreases, causing an increase in current drawn by the motor.

The power supply may include a battery arranged to supply an input voltage to be converted to the output voltage, and the breast pump system may further comprise a power supply control module arranged to detect the input voltage and to control the supply of power in dependence on the detected input voltage to provide the output voltage at a predetermined voltage level. This can avoid the power supply output voltage decreasing as the input voltage provided by the battery decreases over time, improving the system stability by maintaining a more stable output voltage from the power supply.

The breast pump system may further comprise an error indication module arranged to indicate an error condition in response to the detected output voltage remaining below a third threshold voltage for a predetermined time period, the third threshold voltage being higher than the first threshold voltage.

The power supply may be arranged to supply the electrical power to the actuator using pulse width modulation PWM, and the power supply control module may be arranged to determine the PWM duty cycle based on the detected input voltage and the predetermined voltage level. PWM control can allow a high battery input voltage to be reduced to the required output voltage by varying the PWM duty cycle accordingly. This allows the use of batteries with high input voltages relative to the required output voltage, increasing the useful operating time that can be provided by an individual battery before the input voltage falls below the minimum required level.

According to the present invention, there is also provided a method for use in a breast pump system comprising a pump unit, an actuator for driving the pump unit, and a power supply arranged to supply electrical power to a plurality of components including the actuator, the method comprising detecting an output voltage of the power supply, suspending the supply of the electrical power to a predetermined one of the plurality of components in response to the detected output voltage falling below a first threshold voltage, and resuming the supply of the electrical power to the predetermined one of the plurality of components in response to the detected output voltage recovering above a second threshold voltage.

The power supply may include a battery arranged to supply an input voltage to be converted to the output voltage, and the method may further comprise detecting the input voltage, and controlling the supply of power to the actuator in dependence on the detected input voltage to provide the output voltage at a predetermined voltage level.

The breast pump system may further comprise an error indication module, the method further comprising indicating an error in response to the detected output voltage remaining below a third threshold voltage for a predetermined time period, the third threshold voltage being higher than the first threshold voltage.

According to the present invention, there is also provided a breast pump system comprising a power supply arranged to supply electrical power to components in the breast pump system, the power supply including a battery arranged to supply an input voltage to be converted to an output voltage of the power supply, a voltage detecting module arranged to detect the output voltage, and a power supply control module arranged to control the power supply in dependence on the detected input voltage to provide the output voltage at a predetermined voltage level. The power supply may be arranged to supply the electrical power to the electric motor using pulse width modulation PWM, and the power supply control module may be arranged to determine the PWM duty cycle based on the detected input voltage and the predetermined voltage level.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
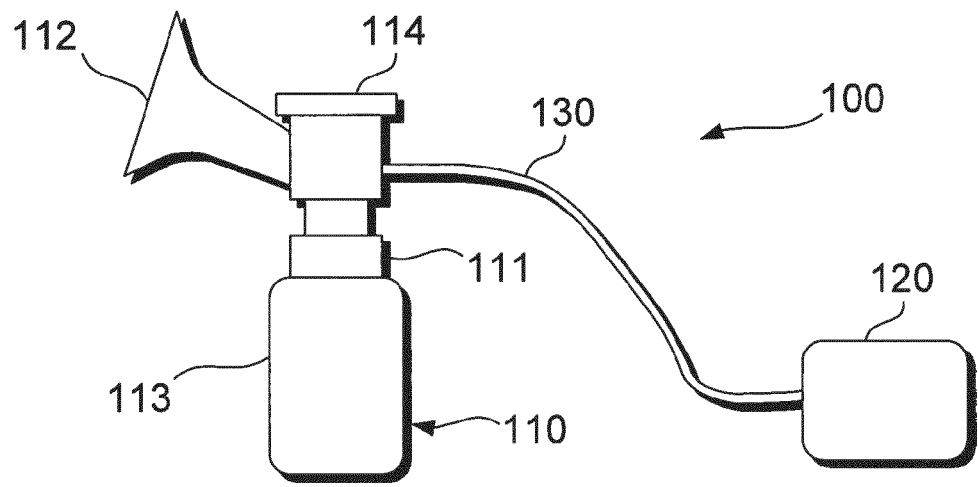
FIG. 1 illustrates a breast pump system, according to an embodiment of the present invention.
Figure 2:
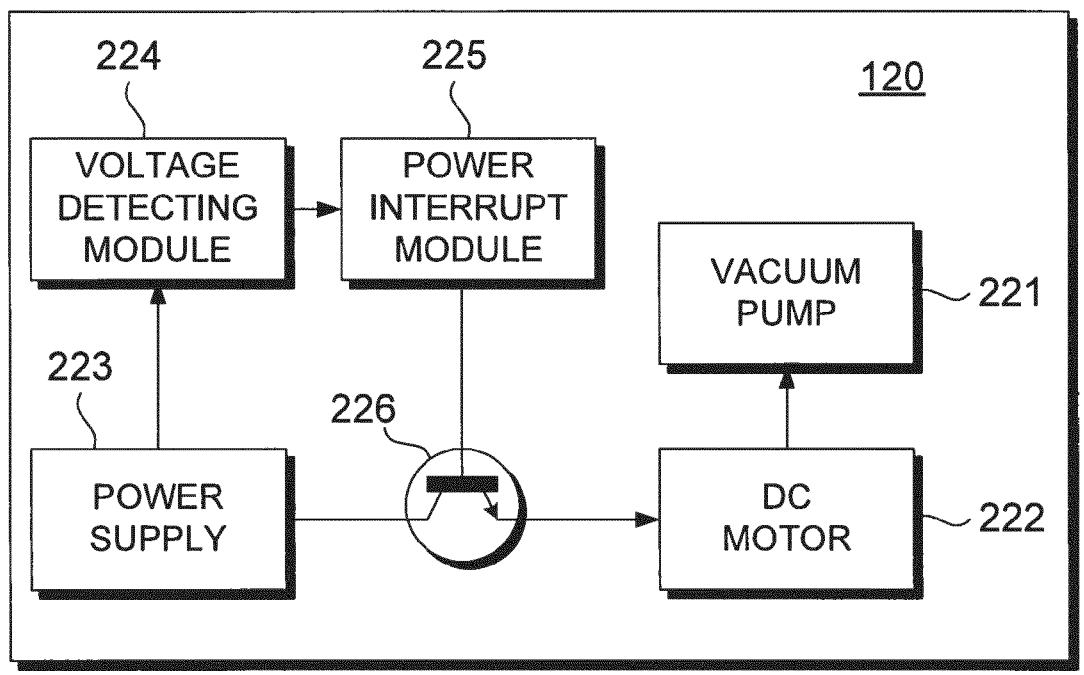
FIG. 2 illustrates the operating unit of the breast pump system of FIG. 1 in more detail.

Referring now to FIGS. 1 and 2, a breast pump system is illustrated according to an embodiment of the present invention. As shown in FIG. 1, the breast pump system 100 includes a breast pump 110, also known as an expression unit, and an operating unit 120 connected by a tube 130 to the breast pump 110. The tube 130 provides a fluid communication between the breast pump 110 and the operating unit 120. The tube 130 may also be used to provide an electrical connection between the breast pump 110 and the operating unit 120. For example, the tube may supply an operating signal or electrical power between the breast pump and the operating unit. Although the operating unit 130 is spaced from the breast pump 110 in the present arrangement, it will be understood that the operating unit may be integrally formed with the breast pump 110.

The breast pump 110 has a main body 111, funnel 112, collection vessel 113 and a diaphragm 114 coupled to the vacuum line 130. The collection vessel 113, or receptacle, collects milk expressed from a user's breast and may take the form of a feeding bottle or bag. The collection vessel 113 is attached to the main body 111 by a screw fitting, although it will be understood that alternative releasable attachment means may be used, such as clips (not shown). The breast-receiving funnel 112 is configured to receive the breast of a user, and has a mouth and a throat. The mouth is open at an outer end of the funnel 112, and the funnel 112 converges from the outer end towards the throat to form a hollow recess in which a breast is received. The main body 111 fluidly connects the funnel 112 to the collection vessel 113. A fluid passageway is formed through the main body 111 from the breast receiving space of the funnel 112 to the collection vessel 113. The main body 111 is formed from an outer shell. The main body 111 is integrally formed with the funnel 112, however it will be understood that the funnel 112 may be detachable The operating unit 120 comprises a vacuum unit and an electric motor for driving the pump unit (not shown in FIG. 1). The electric motor acts as an actuator. The pump unit is configured to generate and release a pressure reduction in a vacuum path. The pressure reduction in the vacuum path may be generated according to a single stroke concept or to a multistroke concept. The means for generating the pressure reduction and the means for releasing the pressure reduction are separate components. In particular, in the present embodiment the pump unit comprises a vacuum pump (not shown in FIG. 1) and a pressure release valve (not shown in FIG. 1). The vacuum pump acts as a pressure reduction means. The pressure release valve acts as a means for releasing a pressure reduction. The vacuum pump is fluidly connected to the main body 111 via the tube 130. The release valve is configured to cyclically open to release the reduction in pressure generated by the vacuum pump. This causes a cyclical pressure differential to be generated. However it will be understood that a different vacuum generating system could also be used. For example, it will be understood that the means for generating the pressure reduction and the means for releasing the pressure reduction may be integrally formed.

A chamber is formed in the main body 111 of the breast pump 110. The chamber is formed along the fluid passageway, and has a vacuum port. The vacuum port communicates with the tube 130 so that the vacuum pump is able to cause a pressure reduction in the chamber.

In the present embodiment, a membrane is received in the chamber. The membrane, or diaphragm, is flexible. The membrane separates the chamber into a first space and a second space. The first space is in fluid communication with the vacuum port. Therefore, a pressure reduction is generated in the first space by the vacuum pump. The second space is in fluid communication with the fluid passageway between the breast receiving space of the funnel 112 and the collection vessel 113. Therefore, the second space is in direct fluid communication with a breast received in the funnel. A one-way valve is disposed between the chamber and the collection vessel 113. When a pressure reduction is generated in the first space, the membrane deforms and is drawn in the direction of the first space. Therefore, a pressure reduction is produced in the second space of the chamber due to the deformation of the membrane. When a breast is received in the mouth of the funnel, a pressure reduction is formed in the funnel which acts on the user's breast and urges milk to be expressed therefrom.

The above arrangement indirectly generates a vacuum at a user's breast. It will be understood that it is also possible to generate a vacuum at a user's breast by omitting the membrane so that a direct fluid connection is formed between the vacuum pump and the funnel. Furthermore, although in the present embodiment separate breast pump and operating units are provided, in other embodiments the breast pump system components such as the collector, funnel, vacuum pump, electric motor and power supply, may be housed in a single body. For example, components of the operating unit may be integrated into the main body of the breast pump, removing the need for a separate operating unit.

The operating unit 120 is illustrated in more detail in FIG. 2, and comprises a vacuum pump 221, direct current (DC) brushed electric motor 222 for driving the vacuum pump 221, power supply 223 for supplying electrical power to the electric motor 222, voltage detecting module 224 for detecting an output voltage of the power supply 223, and a power interrupt module 225. The power supply provides power to a plurality of components in the breast pump system, including the electric motor 222, and the power interrupt module 225 can interrupt the supply of electrical power to one or more predetermined components of the plurality of components when a decrease in an output voltage of the power supply 223 is detected, before the output voltage decreases to an extent that could lead to system instability. Interrupting the supply of electrical power to one or more components in this way can temporarily reduce the load on the power supply so that stable operation of the breast pump system can be maintained.

In the present embodiment the power interrupt module 225 is arranged to interrupt the supply of electrical power to the motor 222 by controlling a switch 226, in this case a Field Effect Transistor (FET), connected between the electric motor 222 and the power supply 223. Hence in the present embodiment the power interrupt module 225 can be referred to as a motor interrupt module. In embodiments where the power supply 223 is arranged to supply power using a Pulse Width Modulation (PWM) method, the FET 226 can be the same FET which is controlled by a PWM controller to switch the supply voltage on or off with the required switching frequency and duty cycle. The motor interrupt module 225 can control the FET 226 directly, as shown in FIG. 2, or can send an interrupt signal to the PWM controller (not shown in FIG. 2). The PWM controller can respond to the interrupt signal by setting the duty cycle to zero. However, in embodiments which are not PWM-controlled, a separate FET 226 or other suitable switch can be provided.

The motor interrupt module 225 is arranged to suspend the supply of the electrical power to the electric motor 222 in response to the detected output voltage falling below a first threshold voltage, and resume the supply of the electrical power to the electric motor 222 in response to the detected output voltage recovering above a second threshold voltage. In this way the motor can be isolated from the power supply when a current spike occurs, avoiding power being wasted in the motor 222 while the situation causing the current spike persists. If the situation causing the current spike still exists when the motor 222 is reconnected after the output voltage has recovered, the output voltage will again decrease below the first threshold voltage and the motor 222 will again be disconnected. The process can continue until the cause of the current spike has been removed, at which point the power supply 223 will continue supplying electrical power to the motor 222 until another current spike occurs, resulting in a decrease in output voltage, or until the system is switched off.

In the present embodiment, the first threshold voltage is less than the second threshold voltage. However, it will be understood that in an alternative embodiment the first threshold voltage is equal to the second threshold voltage.

Although in the present embodiment the power interrupt module is arranged to suspend the supply of electrical power to the motor, in an alternative embodiment the supply of power to one or more other components is suspended, instead of or as well as suspending the supply of power to the motor. For example, the supply of power to a vacuum release valve, such as a solenoid valve, can be interrupted instead of, or as well as, interrupting the supply of power to the motor. The component, or components, for which power is to be suspended when the output voltage falls below the threshold, can be predetermined based on an importance of the component and/or a typical power consumption level of the component. It may only be necessary to suspend the supply of power for a short time, and so the predetermined component or components can be chosen by selecting one or more components that can tolerate a power supply interruption on this timescale. For instance, the supply of power to the motor and/or a vacuum release valve may be interrupted for a short time, for example a few milliseconds, without compromising the safe operation of the breast pump system.

Figure 3:
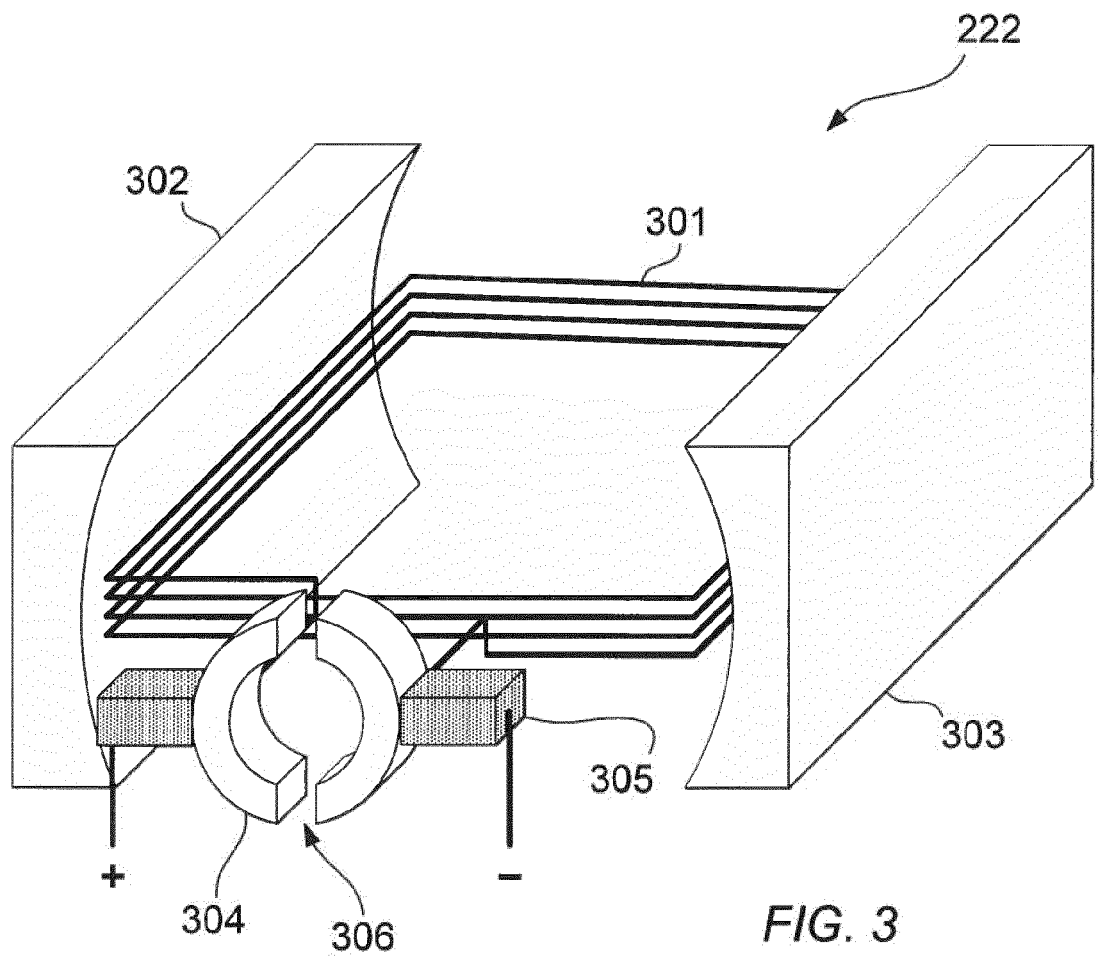
FIG. 3 illustrates a DC brushed electric motor for use in a breast pump system.

The DC brushed electric motor 222 is illustrated in more detail in FIG. 3. The electric motor 222 comprises a coil 301 of wire wrapped around an armature, which is omitted in FIG. 3 for clarity. Permanent magnets 302, 303 are positioned on opposite sides of the coil 301, which is connected to a power supply through commutator segments 304 and carbon brushes 305. The skilled person will be familiar with the operating principles of a DC brushed electric motor, and as such a detailed description will be omitted here to maintain brevity. The commutator segments 304 are separated by an air gap 306. Although two commutator segments 304 are shown in FIG. 3, in general any number of two or more segments may be provided.

Investigations by the inventors have revealed that when a DC brushed electric motor is used in a breast pump system such as the one shown in FIG. 1, current spikes in the electric motor 222 can result in a drop in output voltage of the power supply, due to the increase in power being drawn by the electric motor. Current spikes can occur when mechanical wear of the carbon brushes 305 in the motor 222 causes particles of carbon to detach and cause a short by bridging the gap 306 between adjacent commutator segments 304. Embodiments of the present invention can suspend the supply of electrical power to the motor 222 when a current spike occurs, avoiding power being wasted in the motor 222. The supply of electrical power to the motor 222 can be resumed once the output voltage has recovered. Recovery has been found to typically occur within 1 millisecond (ms) after supply of power to the motor is suspended. Preferably, the output voltage can be sampled at a rate above 1000 samples per second, so that the system can quickly respond and resume the supply of power to the motor as soon as the output voltage has recovered. This avoids the motor being disconnected longer than is necessary.

Although the present embodiments relate to a breast pump system comprising a DC brushed electric motor, it will be understood that the present invention is also applicable to breast pump systems including alternative types of motor. For example, in another arrangement including a DC brushless electric motor, a voltage drop may be caused by a loose wire or a different fault.

Figure 4:
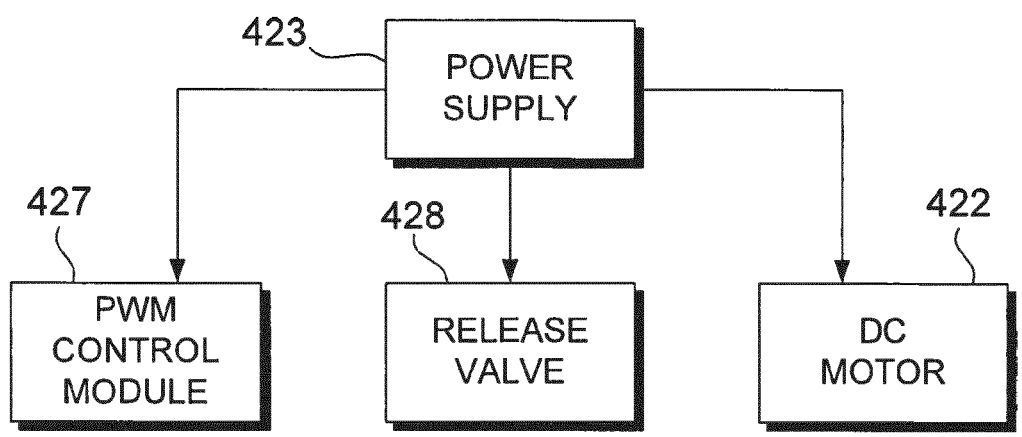
FIG. 4 illustrates a breast pump system in which the same power supply provides electrical power to other components in addition to an electric motor, according to an embodiment of the present invention.

The embodiments of the present invention provide a more stable system in which the same power supply provides power to other components as well as the motor. FIG. 4 illustrates a breast pump system in which a power supply 423 provides power to an electric motor 422, and also to a PWM control module 427 and a release valve 428. The PWM control module 427 can be embodied as a microcontroller, which requires a certain minimum voltage for stable operation. The release valve 428 can also require a minimum voltage for stable operation, which may be the same as or different to the minimum voltage required by the microcontroller. For example, the release vale may be a solenoid release vale that requires a minimum voltage to activate the solenoid and open the valve.

In an embodiment such as the one shown in FIG. 4, the output voltage detected by the voltage detecting module can be the output voltage supplied to another component in the breast pump system by the power supply. For example, the output voltage supplied to the PWM control module 427 or the release valve 428 can be detected instead of the output voltage supplied to the motor 422. The motor interrupt module compares the detected output voltage to a suitable first threshold voltage, which is set to be higher than a minimum voltage required for stable operation by the particular component to which the detected output voltage is supplied. In this way, supply of electrical power to the motor can be suspended before the detected output voltage drops to a low enough level to cause unstable operation of the breast pump system. Hence embodiments of the present invention can improve the stability of a breast pump system in which one power supply provides power to a plurality of components including a DC brushed electric motor.

Figure 5:
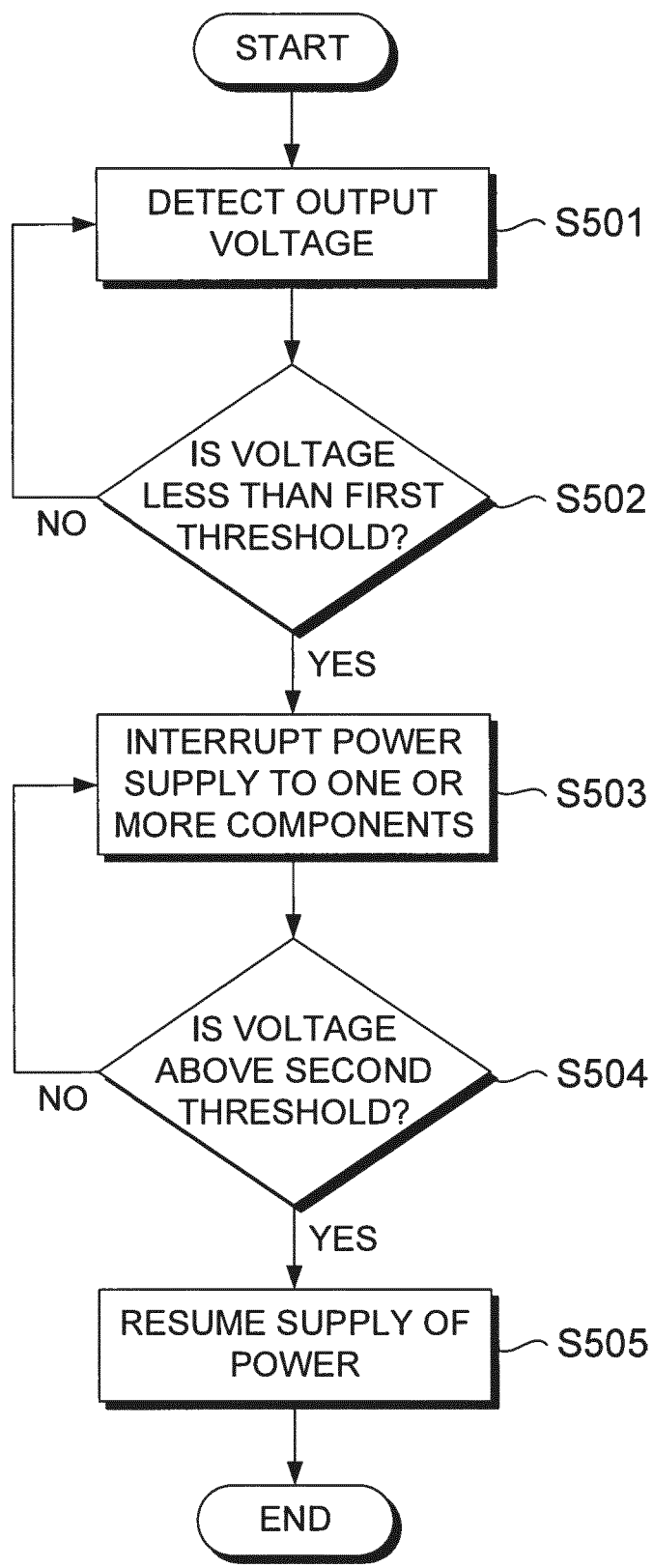
FIG. 5 illustrates a method for use in a breast pump system, according to an embodiment of the present invention.

Referring now to FIG. 5, method for use in a breast pump system including a DC brushed electric motor is illustrated, according to an embodiment of the present invention. The method can be performed by a system such as the one shown in FIG. 2. In a first step S501, an output voltage of a power supply in the breast pump system is detected. Then, in step S502, the detected output voltage is compared to a predetermined first threshold voltage. If the voltage is not less than the first threshold voltage, the process can return to step S501 and continue to monitor the output voltage. On the other hand, if the voltage is less than the first threshold voltage, and process proceeds to step S503 and interrupts the supply of electrical power to a predetermined one of the plurality of components which are powered by the power supply. For example, in a PWM system the supply of power to the electric motor can be interrupted by setting the PWM duty cycle of the motor to zero. Alternatively, a dedicated switch can be provided between the electric motor and power supply to isolate the motor from the power supply.

Next, in step S504, it is checked whether the output voltage has recovered above a predetermined second threshold voltage. If the output voltage has not recovered, the supply of electrical power to the motor continues to be interrupted until the output voltage has recovered. Once it is determined in step S504 that the output voltage has recovered above the second threshold voltage, that is, has increased above the second threshold voltage after decreasing below the first threshold voltage in step S502, the process proceeds to step S505 and resumes the supply of electrical power to the predetermined one of the plurality of components. After resuming the supply of electrical power, the process can return to step S501 to continue to the monitor the output voltage to detect any subsequent voltage drops.

A method as shown in FIG. 5 can reduce power consumption in a breast pump system that includes a DC brushed electric motor. In particular, when a current spike in the DC brushed electric motor occurs that results in a decrease in output voltage of the power supply, due to the surge in power drawn by the motor, this can be detected because the output voltage of the power supply is being monitored. It will be understood that the method shown in FIG. 5 is not limited to a breast pump system that includes a DC brushed electric motor and may relate to alternative types of motor. The supply of electrical power to the motor, and/or one or more other components, can be suspended, allowing stable operation of the other components to continue by setting the first and second threshold voltages to ensure that the power supply continues to provide a minimum required operating voltage to the other components.

Figure 6:
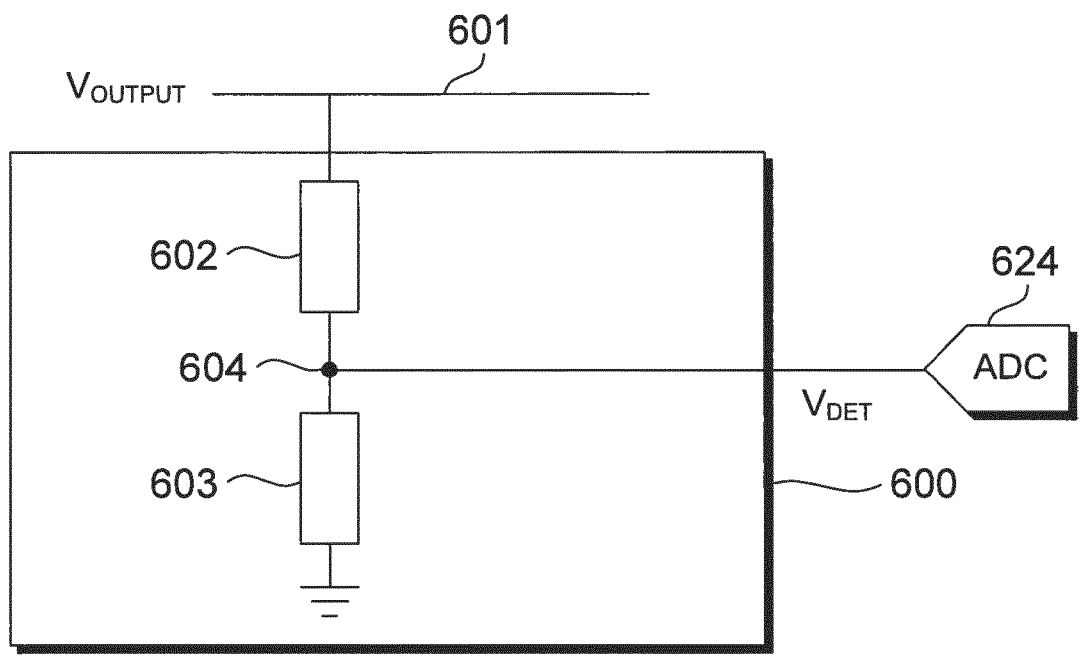
FIG. 6 illustrates a voltage adapting module for adapting an output voltage of a breast pump system power supply, according to an embodiment of the present invention.

Referring now to FIG. 6, a voltage adapting module for adapting an output voltage of a breast pump system power supply is illustrated, according to an embodiment of the present invention. The voltage adapting module can enable use of components in the voltage detecting module that are not able to measure voltages in the range of the normal voltage level of the output voltage. For example, the voltage detecting module can be an analogue-to-digital converter (ADC) 624 as shown in FIG. 6, and any given ADC will have a particular range of input voltages which it is able to measure. The voltage adapting module 600 can reduce the output voltage to a level that lies within the input voltage range of the ADC 624. A voltage adapting module is not required in embodiments where the voltage detecting module is able to detect voltages at a normal operating level of the output voltage.

The voltage adapting module 600 may be configured to reduce an output voltage of a breast pump system power supply. In such an arrangement, the voltage adapting module 600 is connected to an output voltage line 601 of the breast pump system power supply. The output voltage line 601 is directly or indirectly connected to the motor. However, the output voltage line 601 may be connected to another component in the breast pump system by the power supply. Referring back to FIG. 2, the voltage adapting module can be connected between the power supply 223 and the voltage detecting module 224. The voltage adapting module 600 further comprises a first resistor 602 and a second resistor 603 connected in series between the output voltage and a reference voltage, in this case ground. In other embodiments however a different reference voltage may be used, provided the reference voltage is lower than the output voltage. The reduced voltage, which can be referred to as the detection voltage $V_{DET}$, is obtained at a common node 604 of the first and second resistors 602, 603, that is, a node 604 connected between the first and second resistors 602, 603. The voltage detecting module, in this embodiment an ADC 624, is connected to the node 604 to receive the reduced voltage.

When the reduced voltage is detected, as opposed to directly detecting the output voltage, the threshold voltage used for comparison in the motor interrupt module can be a corresponding reduced threshold voltage. That is, a reduced threshold voltage can be set such that when the output voltage is at the threshold voltage, the reduced voltage is at the reduced threshold voltage. If, for example, the desired threshold voltage for the output voltage is higher than a minimum required voltage for stable operation of other components in the breast pump system, it may be possible for the reduced threshold voltage to be lower than the minimum required voltage. It will be appreciated that this will depend on the extent to which the output voltage is reduced by the voltage adapting module 600.

Figure 7:
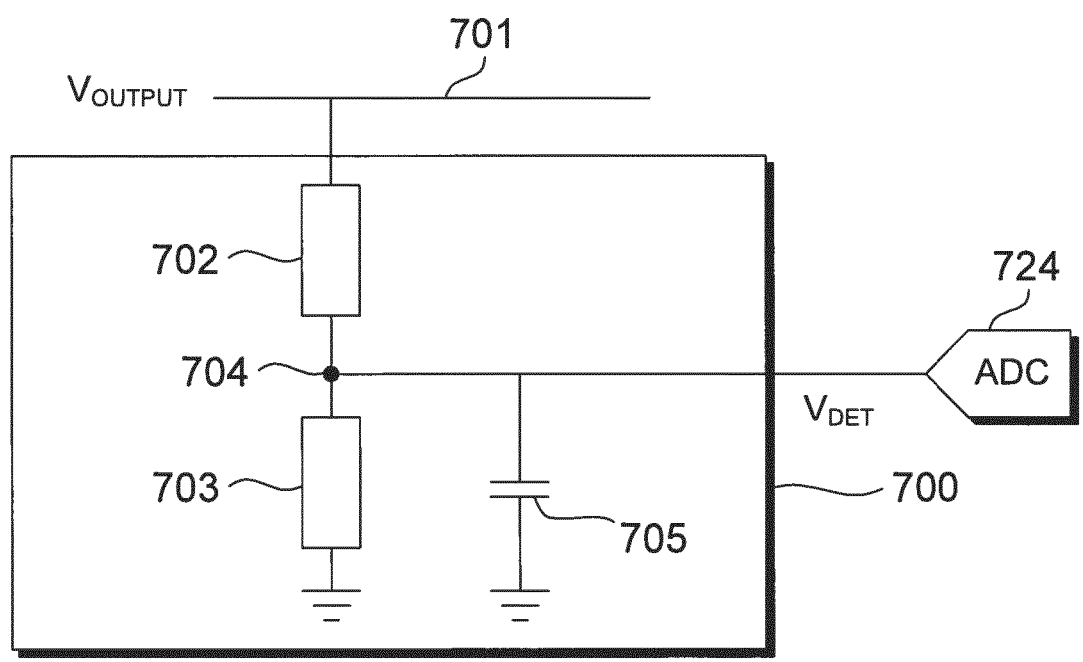
FIG. 7 illustrates a voltage adapting module including a capacitor as a low-pass filter, according to an embodiment of the present invention.

Referring now to FIG. 7, a voltage adapting module including a capacitor as a low-pass filter is illustrated, according to an embodiment of the present invention. The voltage adapting module 700 is similar to the voltage adapting module 600 of FIG. 6, and comprises first and second resistors 702, 703 connected in series between an output voltage line 701 and a reference voltage, a common node 704 of the resistors 702, 703 being connected to a voltage detecting module 724. However, the voltage adapting module 700 of FIG. 7 further comprises a capacitor 705 connected between the node 704 and a reference voltage, which may be the same reference voltage to which the second resistor 703 is connected, or a difference reference voltage. The output voltage line 701 is directly or indirectly connected to the motor. However, the output voltage line 601 may be connected to another component in the breast pump system by the power supply.

The speed with which the voltage detecting module 724, and hence the motor interrupt module, responds to changes in the reduced voltage $V_{DET}$ can be determined by the capacitance of the capacitor 705, which functions as a low-pass filter. A smaller capacitance will provide a shorter response time, whereas a higher capacitance will provide a longer response time. The capacitor can filter out high-frequency noise in the reduced voltage $V_{DET}$. For example, in a PWM-controlled system the output voltage is rapidly switched between a certain voltage level and zero volts. The capacitor can smooth out this switching variation in the reduced voltage by filtering out signals at the PWM switching frequency. This ensures that the motor interrupt module does not suspend the supply of electrical power to the motor during every switching cycle, when the output voltage is temporarily switched to zero volts. Although a capacitor 705 is used as a filter in the voltage adapting module 700 of FIG. 7, it will be appreciated that other types of filter could be substituted in other embodiments. For example, in one embodiment the capacitor could be replaced with an active low-pass filter comprising an operational amplifier with a feedback connection between the output and the inverted input. In some embodiments however the filtering may not be required. For example, the ADC 724 may have a sampling rate low enough that variations on the PWM switching timescale cannot be detected, or other components used in the motor interrupt module may not operate at high enough speeds to be capable of responding to variations on the PWM switching timescale.

Figure 8:
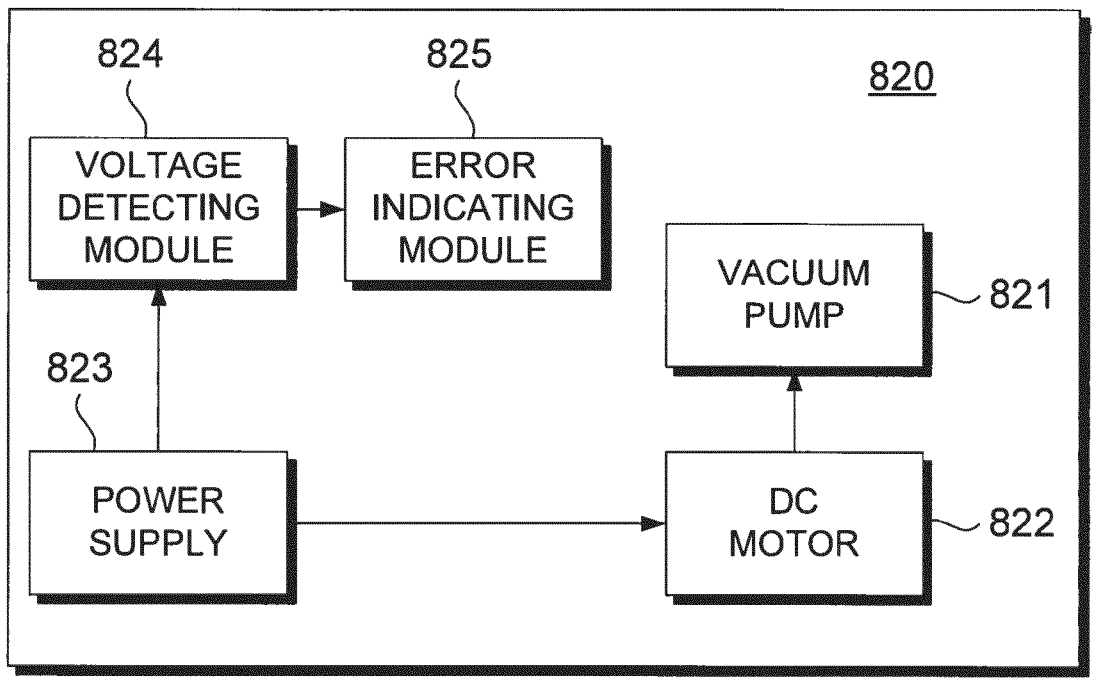
FIG. 8 illustrates a breast pump system including an error indicating module for indicating when an electric motor is approaching the end of its operating life, according to an embodiment of the present invention.

Referring now to FIG. 8, a breast pump system is illustrated according to an embodiment of the present invention. The breast pump system includes an error indicating module 825 for indicating when an electric motor is drawing too much current for too long. This may indicate when an electric motor is approaching the end of its operating life. In the present embodiment the error indicating module 825 is included in an operating unit 820 similar to the operating unit of FIG. 2, comprising a vacuum pump 821, electric motor 822, such as a DC brushed electric motor, power supply 823, voltage detecting module 824, and motor interrupt module (not shown in FIG. 8). In other embodiments the error indicating module 825 can be provided in the collecting unit, or the components of the operating unit 820 and a collecting unit can be integrated into the breast pump main body.

The error indicating module 825 is connected to the voltage detecting module 824, which may be the same voltage detecting module to which the motor interrupt module (not shown) is connected, or may be a separate voltage detecting module. The error indicating module 825 compares the detected output voltage to a third threshold voltage, which can be higher than the first threshold voltage used by the motor interrupt module. It is assumed that a continued low voltage condition is the result of a higher current being drawn by the motor as it nears the end of its operating lifetime, since the carbon brushes have been heavily worn and their resistance has decreased. Therefore if the error indicating module 825 determines that the detected output voltage has been below the third threshold voltage for at least a predetermined time period, the error indicating module 825 indicates an error condition to signal that the motor is nearing the end of its operating lifetime. The third threshold voltage can be chosen to be a level that typically occurs a certain time before failure of the motor, for example one month before failure under normal use conditions, to give a user of the system time to replace the motor or obtain a new breast pump system. The error indication can, for example, be provided visually through a display or by illuminating a light emitting diode (LED), or can be provided audibly through a loudspeaker.

Figure 9:
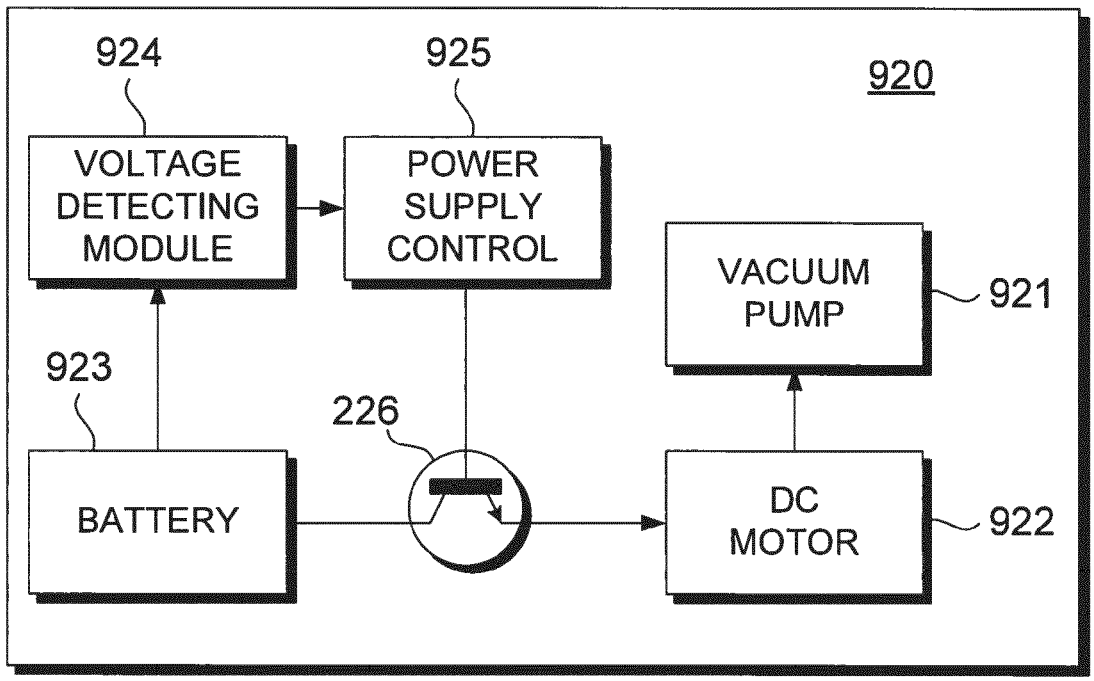
FIG. 9 illustrates a breast pump system in which the power supply includes a rechargeable battery, and a power supply controller controls the power supply based on a detected input voltage provided by the battery, according to an embodiment of the present invention.

Referring now to FIG. 9, a breast pump system is illustrated according to an embodiment of the present invention. The breast pump system includes a power supply control module 925 to control the power supply in dependence on a detected input voltage to provide the output voltage at a predetermined voltage level. In the present embodiment the error indicating module 925 is included in an operating unit 920 similar to the operating unit of FIG. 2, comprising a vacuum pump 921, an electric motor 922, such as a DC brushed electric motor, a power supply 923, such as a battery, a voltage detecting module 924, and a motor interrupt module (not shown in FIG. 9). In some embodiments the power supply control module 925 can be provided in a breast pump system that does not include a motor interrupt module. For example, the power supply control module could be applied to systems that do not use DC brushed electric motors, in which a motor interrupt module is not required.

In more detail, the power supply includes a rechargeable battery 923 arranged to provide an input voltage to be converted to an output voltage of the power supply. The voltage detecting module 924 is arranged to detect the input voltage provided by the rechargeable battery, which may also be referred to as the battery voltage. The power supply control module 925 is connected to the voltage detecting module 924 and is arranged to control the power supply in dependence on the detected input voltage. The input voltage provided by the rechargeable battery can decrease significantly as the stored energy in the battery is drained over time, and by monitoring the input voltage the power supply control module 925 can control the power supply as necessary to ensure that a stable operating voltage is maintained. In the present embodiment the power supply is controlled using PWM, by switching a FET 226 connected between the power supply 923 and electric motor 922. The power supply control module 925 is arranged to obtain a PWM duty cycle D as:

$$D = V_O / V_{IN}$$

where $V_O$ is the desired output voltage, and $V_{IN}$ is the input voltage provided by the battery. If the detected input voltage changes over time, the power supply control module 925 can determine a new duty cycle accordingly and control the FET 226 based on the new duty cycle to provide electrical power to the motor 922 at the desired output voltage.

The present embodiments relate to a breast pump system comprising a single power supply. However, it will be understood that the present invention is also applicable to breast pump systems including two or more power sources. For example, in another arrangement including a DC brushed electric motor, a second power source, more specific a capacitor, is connected to the printed circuit board (PCB) to locally buffer the power supply to reduce the spike. In some embodiments, instead of using PWM to convert the input voltage to the output voltage, a breast pump system may further include a DC-to-DC converter, for example a linear regulator or switched-mode power supply, for converting a battery input voltage to a desired output voltage. The power supply control module can control the DC-to-DC converter accordingly, based on the detected input voltage.

Figure 10:
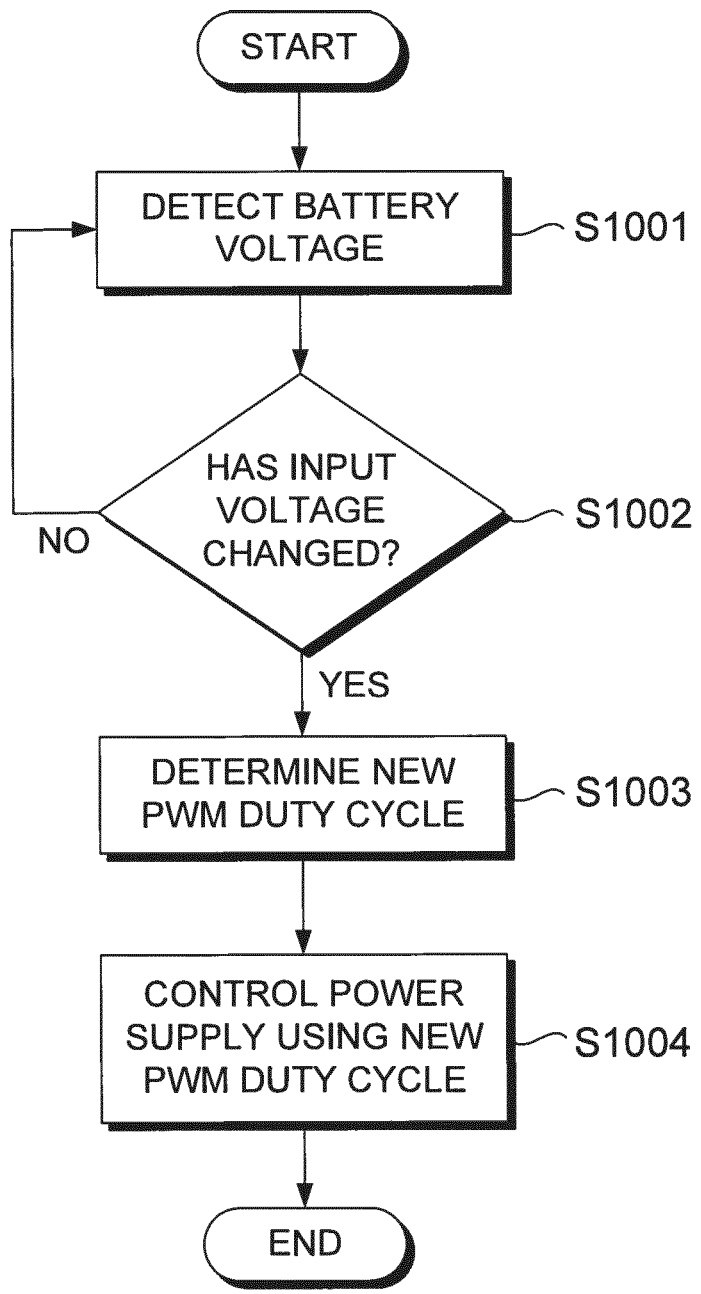
FIG. 10 illustrates a pulse-width modulation PWM method for controlling the power supply based on the detected input voltage provided by the battery, according to an embodiment of the present invention.

Referring now to FIG. 10, a pulse-width modulation PWM method for controlling a breast pump power supply based on the detected input voltage provided by a rechargeable battery is illustrated, according to an embodiment of the present invention. First, in step S1001, the input voltage provided by the battery is detected. Then, in step S1002 it is determined whether the input voltage has changed since the previous measurement. Here, it may be checked whether the input voltage has changed by any amount, or has changed by more than a predetermined amount. If the input voltage has not changed, the process returns to step S1001 and continues to monitor the input voltage. If however the input voltage has changed, then in step S1003 a new duty cycle is calculated that can provide the desired output voltage given the current value of the input voltage, as described above with reference to FIG. 9. Next, in step S1004 the power supply is controlled using the new PWM duty cycle, to continue providing power at the desired output voltage despite the change in input voltage.

Although in the above described embodiments the pump unit is provided with separate means for generating the pressure reduction in the vacuum path and releasing the pressure reduction in the vacuum path, it will be understood that they may be integrated. In another embodiment, the pump unit comprises a piston slidably received in a piston chamber or cylinder. The piston acts as a reciprocating element. The piston forms a fluid seal in the chamber. The piston chamber forms part of the vacuum path. The piston is reciprocally operated, for example, by a crankshaft and a motor. When the piston is drawn along the piston chamber, the movement of the piston acts to generate a pressure reduction in the vacuum path. Therefore, a vacuum may be produced at the user's breast. When the piston moves in the opposite on its return stroke the pressure reduction in the chamber is released. However, in the event that the piston becomes stuck or the motor fails, for example, then the piston will not release the pressure reduction in the vacuum path. That is, the pump unit will fail to release the pressure reduction in the vacuum path. If this occurs, then the leakage aperture provided in the vacuum path will allow a controlled release of the pressure reduction in the vacuum path.

In the above embodiment, it will be understood that the vacuum path is formed between the piston and a user's breast when the breast pump system is assembled and a user's breast is received in the funnel. The pump unit may be disposed in the operating unit or may be housed in the breast pump.

In another embodiment, the pump unit is formed by the membrane and a means of mechanically deforming the membrane. The membrane acts as a reciprocating element. For example, a rod may be attached to the deformable membrane which is movable in a reciprocal manner by an electric motor. With such an arrangement the deformation of the membrane from its neutral condition generates a pressure reduction in the vacuum path. Subsequently, the return of the membrane to its neutral condition releases the pressure reduction in the vacuum path. In this embodiment it will be understood that the vacuum path is formed between the membrane and a user's breast when the breast pump system is assembled and a user's breast is received in the funnel. However, in the event that the membrane does not return to its neutral condition, for example due to failure of the electric motor, then the membrane will not release the pressure reduction in the vacuum path. That is, the pump unit will fail to release the pressure reduction in the vacuum path. If this occurs, then the leakage aperture provided in the vacuum path will allow a controlled release of the pressure reduction in the vacuum path. The membrane may be the membrane described in the above embodiments or may be another membrane disposed separately.

In the above two embodiments, it will be understood that no pressure release valve is required because the reduction in pressure is released by the valve or membrane returning to its neutral position.

It will be appreciated that although embodiments of the present invention have been described and illustrated as including certain elements, which may be referred to as components, modules or units, the structures shown are exemplary only. The elements illustrated can be physically separate hardware components, or can be integrated into a single module performing the functionality of the individual modules shown in any of the embodiments. For example, in FIG. 2 the description of a voltage detecting module 224 and motor interrupt module 225 does not imply that these modules are physically separate. In an embodiment, both modules can be embodied in a single chip, including an ADC as the voltage detecting module 224 and additional hardware arranged to perform the function of the motor interrupt module 225. In some embodiments the functions of one or more components may be performed by a processor executing software instructions.

It will also be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump system comprising:
   a pump unit;
   a DC motor for driving the pump unit;
   a power supply configured to supply electrical power to a plurality of components including the DC motor;
   a switch connected between the power supply and the DC motor;
   a voltage detecting module configured to detect an output voltage of the power supply; and
   a power interrupt module connected to the switch and configured to suspend the supply of the electrical power to the DC motor only, while continuing to supply power to at least one other of said plurality of components, when a current spike occurs in the DC motor by opening the switch in response to the detected output voltage falling below a first threshold voltage, to disconnect the DC motor from the power supply, and also configured to automatically resume, without intervening action by a user of the system, the supply of the electrical power to the DC motor by closing the switch in response to the detected output voltage recovering above a second threshold voltage, to connect the DC motor to the power supply.

2. The breast pump system of claim 1, wherein the power supply is configured to supply the electrical power to the DC motor using pulse width modulation PWM and the power interrupt module is configured to suspend the supply of the electrical power to the DC motor by setting the PWM duty cycle to zero.

3. The breast pump system of claim 1, wherein the power interrupt module includes an analogue-to-digital converter ADC for measuring voltages within a predetermined input voltage range, the breast pump system further comprising:
   a voltage adapting module for adapting the output voltage to an adapted voltage lying within the input voltage range of the ADC,
   wherein the power interrupt module is configured to detect the output voltage falling below the first threshold voltage by detecting the adapted voltage falling below a corresponding adapted threshold voltage.

4. The breast pump system of claim 3, wherein the voltage adapting module comprises first and second resistors connected in series between the output voltage and a first reference voltage to obtain the adapted voltage at a node between the first and second resistors.

5. The breast pump system of claim 1, wherein the output voltage is the voltage supplied to the DC motor.

6. The breast pump system of claim 1, wherein the output voltage is a voltage supplied to one or more of the plurality of components, and the first threshold voltage is higher than a minimum operating voltage required by the one or more components.

7. The breast pump system of claim 6, wherein the one or more other components includes a valve for releasing a vacuum generated by the vacuum pump, and/or a pulse width modulation PWM controller for controlling the actuator.

8. The breast pump system of claim 1, further comprising:
an error indication module configured to indicate an error condition in response to the detected output voltage.

9. The breast pump system of claim 1, wherein the power supply includes a battery arranged to supply an input voltage to be converted to the output voltage, the breast pump system further comprising:
a power supply control module arranged to detect the input voltage and to control the supply of power in dependence on the detected input voltage to provide the output voltage at a predetermined voltage level.

10. The breast pump system of claim 9, further comprising: an error indication module arranged to indicate an error condition in response to the detected output voltage remaining below a third threshold voltage for a predetermined time period, the third threshold voltage being higher than the first threshold voltage.

11. The breast pump system of claim 9, wherein the power supply is arranged to supply the electrical power to the actuator using pulse width modulation PWM, and the power supply control module is arranged to determine the PWM duty cycle based on the detected input voltage and the predetermined voltage level.

12. A breast pump system comprising: a pump unit;
a DC motor for driving the pump unit;
a power supply configured to supply electrical power to a plurality of components including the DC motor;
a switch connected between the power supply and the DC motor;
a voltage detecting module arranged to detect an output voltage of the power supply; and
a power interrupt module connected to the switch and configured to suspend the supply of the electrical power to the DC motor only, while continuing to supply power to at least one other of said plurality of components, when a current spike occurs in the DC motor by opening the switch in response to the detected output voltage falling below a first threshold voltage, to disconnect the DC motor from the power supply, and also configured to automatically resume, without intervening action by a user of the system, the supply of the electrical power to the DC motor by closing the switch in response to the detected output voltage recovering above a second threshold voltage, to connect the DC motor to the power supply,
wherein the power interrupt module is further configured to sample the output voltage with a sampling rate higher than about 1000 samples per second.

* * * * *